US00PP31685P2

(12) United States Plant Patent

Mowrey et al.

(10) Patent No.: US PP31,685 P2

(45) Date of Patent: Apr. 21, 2020

(54) BLUEBERRY PLANT VARIETY NAMED 'DRISBLUESIXTEEN'

(50) Latin Name: ***Vaccinium corymbosum* L.**
Varietal Denomination: DrisBlueSixteen

(71) Applicant: Driscoll's, Inc., Watsonville, CA (US)

(72) Inventors: Bruce D. Mowrey, Watsonville, CA (US); Brian K. Caster, Watsonville, CA (US); Jennifer K. Izzo, Watsonville, CA (US); Marta C. Baptista, Watsonville, CA (US)

(73) Assignee: Driscoll's, Inc., Watsonville, FL (US)

( * ) Notice: Subject to any disclaimer, the term of this patent is extended or adjusted under 35 U.S.C. 154(b) by 0 days.

(21) Appl. No.: 16/350,020

(22) Filed: Sep. 13, 2018

(51) Int. Cl.
*A01H 5/08* (2018.01)
*A01H 6/36* (2018.01)

(52) U.S. Cl.
USPC ..... Plt./157
CPC ..... *A01H 6/368* (2018.05)

(58) Field of Classification Search
USPC ..... Plt./157
CPC ... A01H 5/08; A01H 5/00; A01H 5/02; A01H 4/00; A01H 6/36; A01H 6/368
See application file for complete search history.

(56) References Cited

U.S. PATENT DOCUMENTS

| | | | |
|---|---|---|---|
| PP6,699 | P | 3/1989 | Wood |
| PP11,807 | P2 | 3/2001 | Lyrene |
| PP12,783 | P2 | 7/2002 | Lyrene |
| PP20,436 | P2 | 10/2009 | Caster et al. |
| PP20,449 | P2 | 11/2009 | Caster et al. |
| PP20,488 | P2 | 11/2009 | Caster et al. |
| PP24,407 | P3 | 4/2014 | Caster et al. |
| PP24,489 | P3 | 5/2014 | Caster et al. |
| PP24,568 | P3 | 6/2014 | Caster et al. |
| PP24,569 | P3 | 6/2014 | Caster et al. |
| PP24,605 | P3 | 7/2014 | Caster et al. |
| PP26,287 | P3 | 1/2016 | Caster et al. |
| PP26,451 | P3 | 3/2016 | Caster et al. |
| PP26,537 | P3 | 3/2016 | Caster et al. |
| PP26,643 | P3 | 4/2016 | Caster et al. |
| PP26,748 | P3 | 5/2016 | Caster et al. |
| PP27,622 | P3 | 1/2017 | Caster et al. |
| PP28,933 | P2 | 2/2018 | Caster et al. |

OTHER PUBLICATIONS

Google English Translation from Spanish to English of SAG Ministerio de Agricultura retrieved on Aug. 14, 2019, retrieved from the Internet at https://www.google.com/search?q=translation&rlz=1C1GCEB_enUS773US773&oq=translation&aqs=chrome..69i57j015.2750j0j1&sourceid=chrome&ie=UTF-8, one page (Year: 2019).*

SAG Minsterio de Agricultura Declaraciones de Existencia de Plantas Frutales al Expendio 2001-2017, retrieved on Aug. 14, 2019, 2 pp. (Year: 2017).*

Upov Pluto Plant Variety Database Jul. 31, 2019, retrieved on Aug. 14, 2019, retrieved from the Internet at https://www.upov.int/pluto/en/index.jsp, one page. (Year: 2019).*

Caster et al., Unpublished U.S. Appl. No. 16/350,021, filed Sep. 13, 2018, titled "Blueberry Plant Variety Named 'DrisBlueSeventeen'".

Caster et al., Unpublished U.S. Appl. No. 16/350,012, filed Sep. 12, 2018, titled "Blueberry Plant Variety Named 'DrisBlueEighteen'".

Wiechers, J. D., SAG Letter No. 7271/2019 dated Dec. 3, 2019, 3 pages. English language translation attached.

* cited by examiner

*Primary Examiner* — June Hwu

(74) *Attorney, Agent, or Firm* — Morrison & Foerster LLP

(57) ABSTRACT

A new and distinct variety of blueberry plant named 'DrisBlueSixteen', particularly selected for its ability to flower in summer and fruit in fall on current season's growth, average to - large fruit size, good fruit flavor, and its very erect plants that fruit on exposed tops of canes, is disclosed.

7 Drawing Sheets

Latin name:

Botanical classification: *Vaccinium corymbosum* L.

Varietal denomination: The varietal denomination of the claimed variety of blueberry plant is 'DrisBlueSixteen'.

BACKGROUND OF THE INVENTION

Blueberry plants are perennial flowering plants with indigo-colored berries from the section *Cyanococcus* within the genus *Vaccinium*. Many commercially sold species with English common names, including blueberry, are currently classified in section *Cyanococcus* of the genus *Vaccinium* and come predominantly from North America. Many North American native species of blueberries are grown commercially in the Southern Hemisphere in Australia, New Zealand, and South American nations.

*Vaccinium corymbosum*, the northern highbush blueberry, is a North American species of blueberry which has become a food crop of significant economic importance. It is native to eastern Canada and the eastern and southern United States, from Ontario east to Nova Scotia and south as far as Florida and eastern Texas. It has been naturalized in Europe, Japan, New Zealand, and the Pacific Northwest of North America. Other common names include blue huckleberry, tall huckleberry, swamp huckleberry, high blueberry, and swamp blueberry.

Blueberries are usually erect, prostrate shrubs that can vary in size from approximately four inches to approximately 13 feet in height. In the commercial production of blueberries, the smaller species are known as "lowbush blueberries", while the larger species are known as "highbush blueberries".

Blueberry bushes typically bear fruit in the middle of the growing season. However, fruiting times can be affected by local conditions such as altitude and latitude. As such, peak crop can vary from May to August in the northern hemisphere, depending upon these conditions.

Blueberries are a popular fruit that is typically consumed as fresh fruit, individually quick frozen (IQF) fruit, or in prepared foods, such as purées, juices, jellies, jams, baked goods, snack foods, and cereals.

Blueberry is an important and valuable fruit crop. Accordingly, there is a need for new varieties of blueberry plant. In particular, there is a need for improved varieties of blueberry plant that are stable, high yielding, and agronomically sound.

SUMMARY OF THE INVENTION

In order to meet these needs, the present invention is directed to an improved variety of blueberry plant. In particular, the invention relates to a new and distinct variety of blueberry plant (*Vaccinium corymbosum* L.), which has been denominated as 'DrisBlueSixteen'.

Blueberry plant variety 'DrisBlueSixteen' was discovered in Santa Cruz County, Calif. in 2009 and originated from a cross between the proprietary female parent blueberry plant '127D 2' (unpatented) and the proprietary male parent blueberry plant 'DrisBlueOne' (U.S. Plant Pat. No. 20,449). The original seedling of the new variety was first asexually propagated via cuttings at a nursery in Santa Cruz County, Calif. in 2010. 'DrisBlueSixteen' was subsequently asexually propagated via softwood cuttings and underwent further testing at ranches in Santa Cruz County and Ventura County, Calif. for nine years (2009 to 2017). The present variety has been found to be stable and reproduce true to type through successive asexual propagations via softwood cuttings.

'DrisBlueSixteen' exhibits the following distinguishing characteristics when grown under normal horticultural practices in Santa Cruz County, Calif.:

1. Upright growth habit;
2. Early fruit maturation; and
3. Fruiting on one-year-old and current season's shoots.

'DrisBlueSixteen' was selected for its ability to flower in summer and fruit in fall on current season's shoots, average to large fruit size, good fruit flavor, and its very erect plants that fruit on exposed tops of canes.

BRIEF DESCRIPTION OF THE DRAWINGS

This new blueberry plant variety is illustrated by the accompanying photographs. The colors shown are as true as can be reasonably obtained by conventional photographic procedures. The photographs are of plants that are 3.5 years old, unless otherwise specified.

DETAILED BOTANICAL DESCRIPTION

Figure 1:
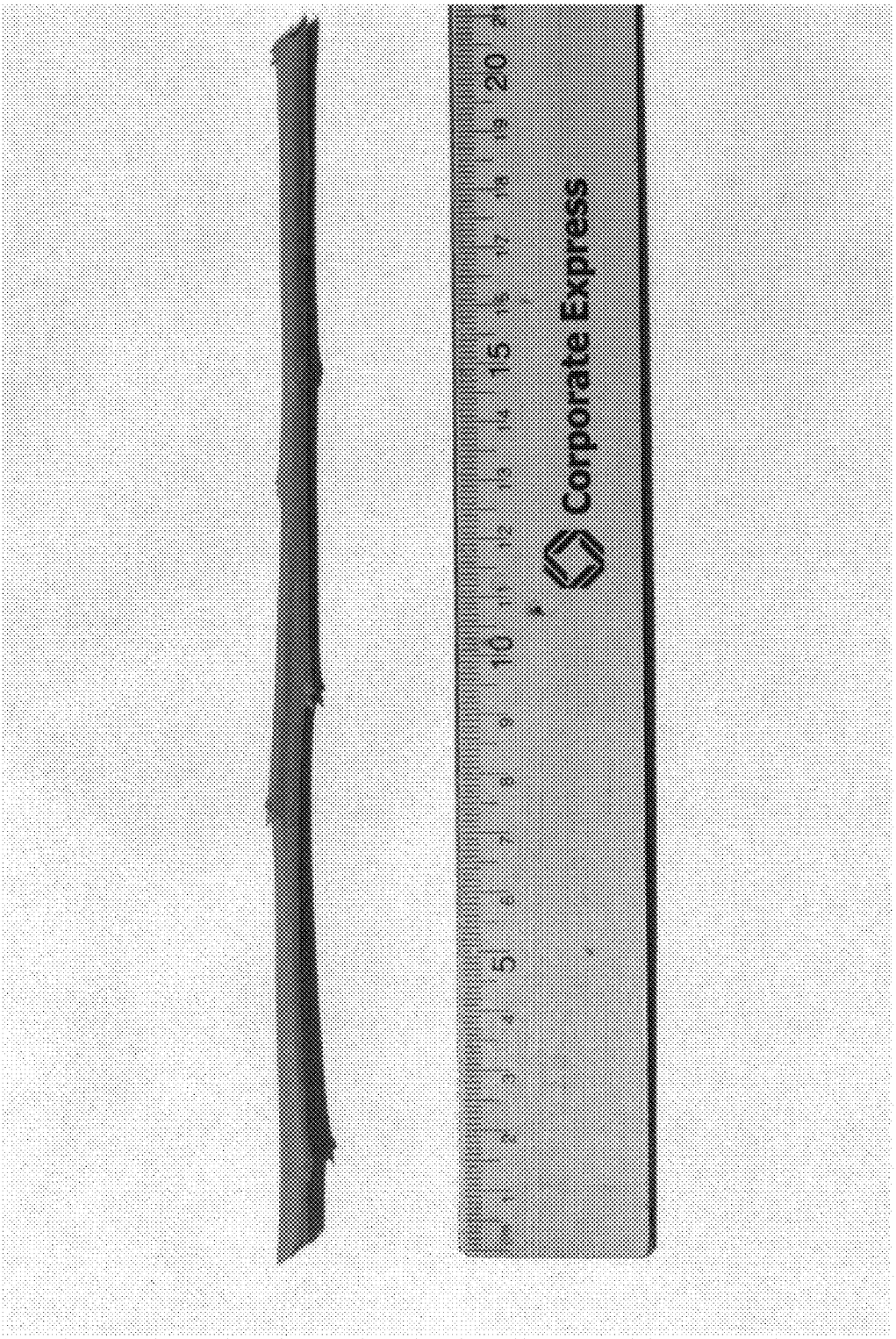
FIG. 1 illustrates a section of a current season one-year-old cane of variety 'DrisBlueSixteen'.
Figure 2:
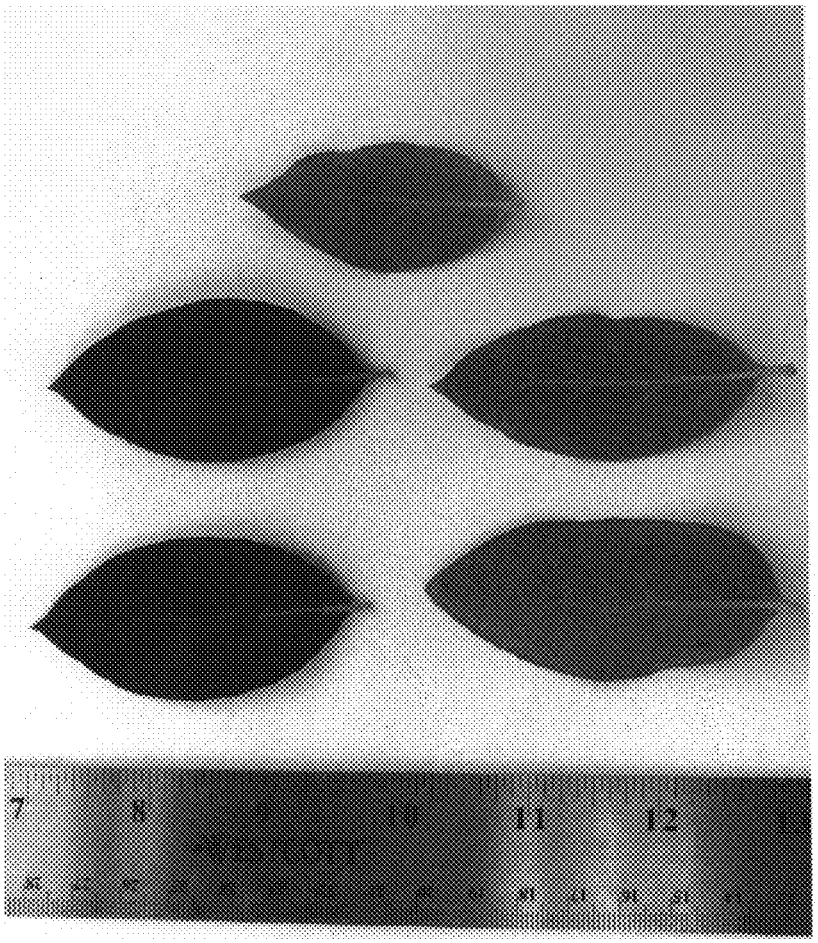
FIG. 2 illustrates leaves of variety 'DrisBlueSixteen'. The upper leaf surfaces are shown on the left side and the lower leaf surfaces are shown on the top and right sides.
Figure 3:
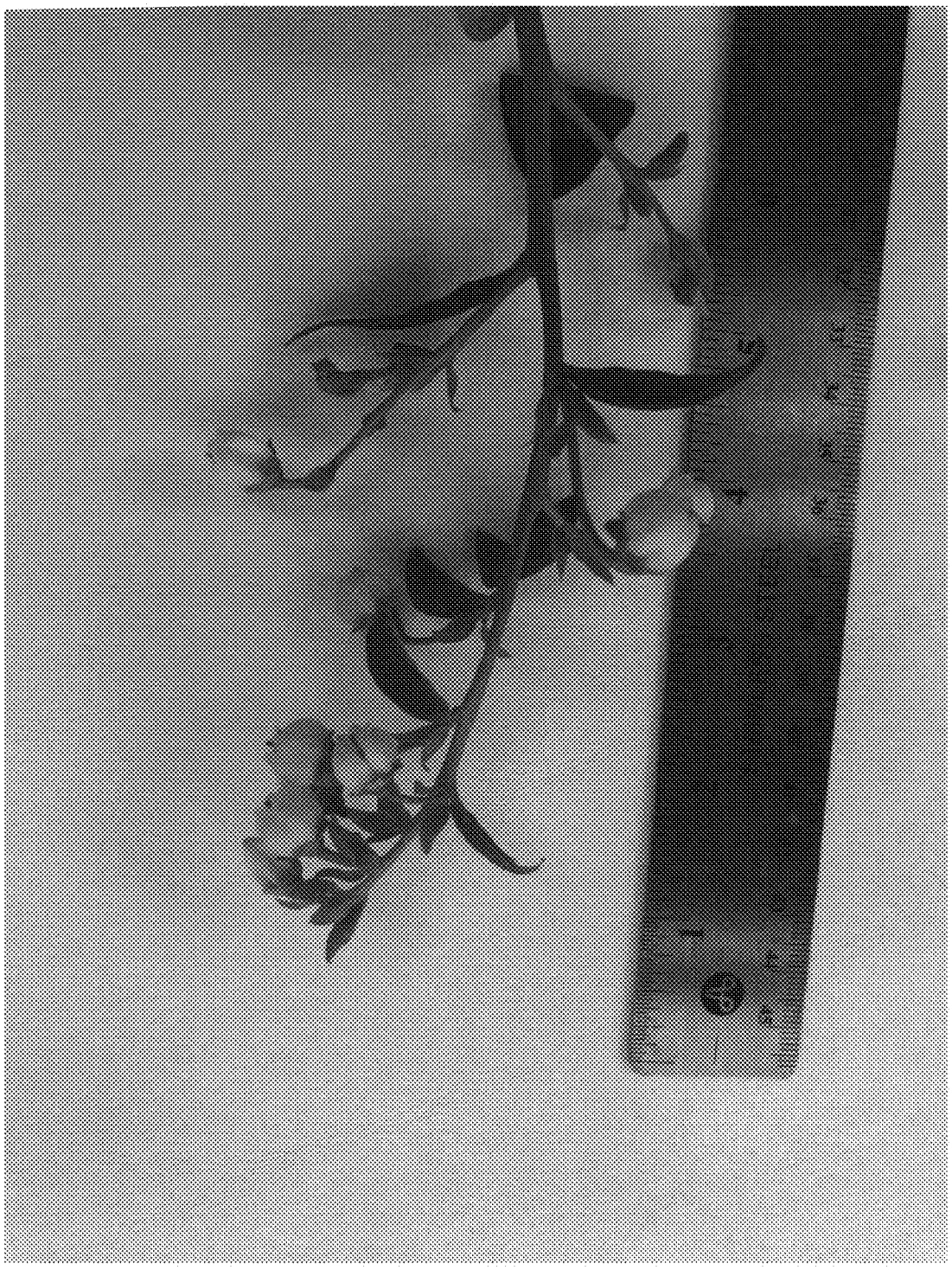
FIG. 3 illustrates flowers of variety 'DrisBlueSixteen'.
Figure 4:
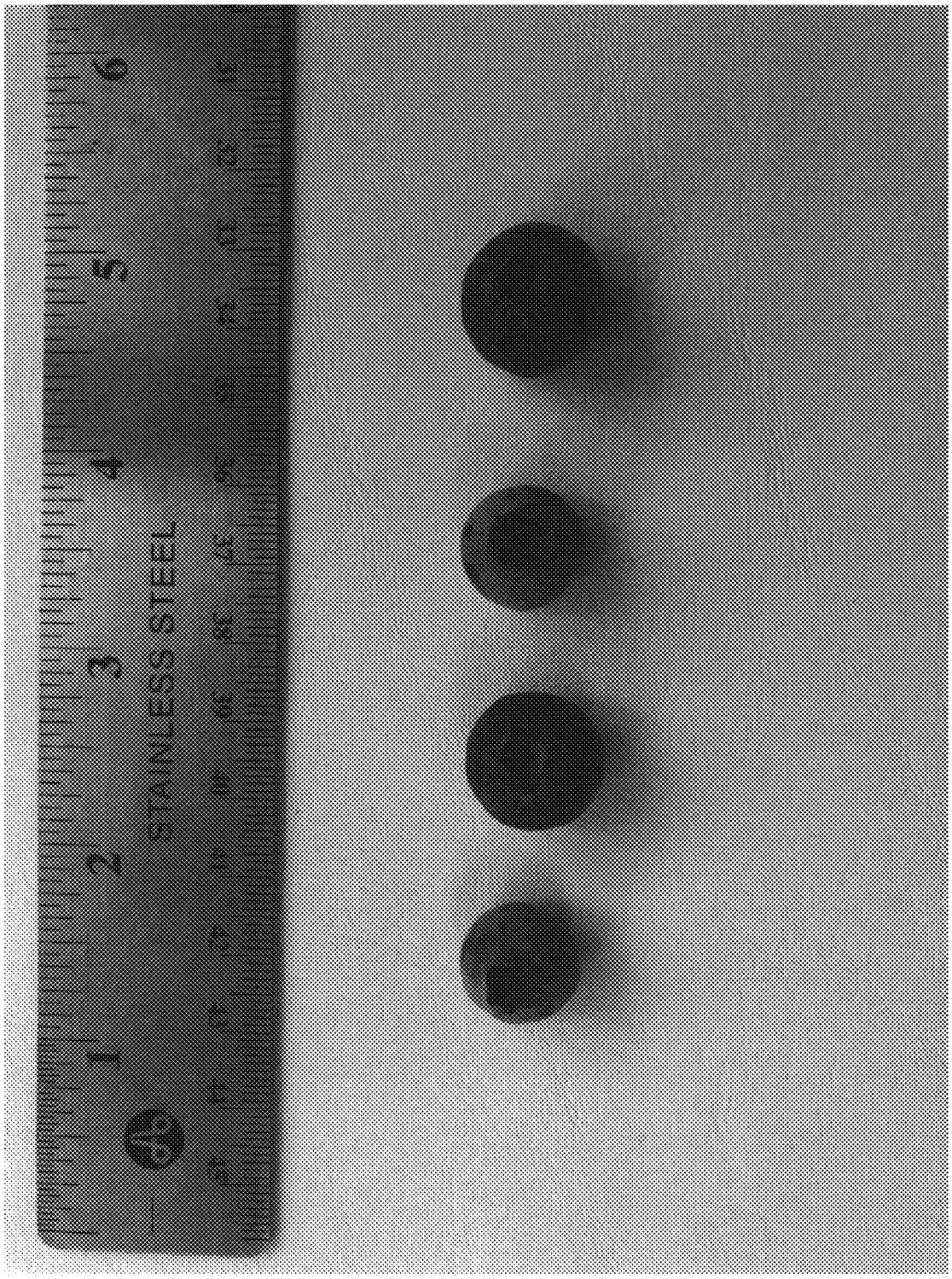
FIG. 4 illustrates whole fruit of variety 'DrisBlueSixteen'. The view of the whole fruit is from the calyx end of fruit.
Figure 5:
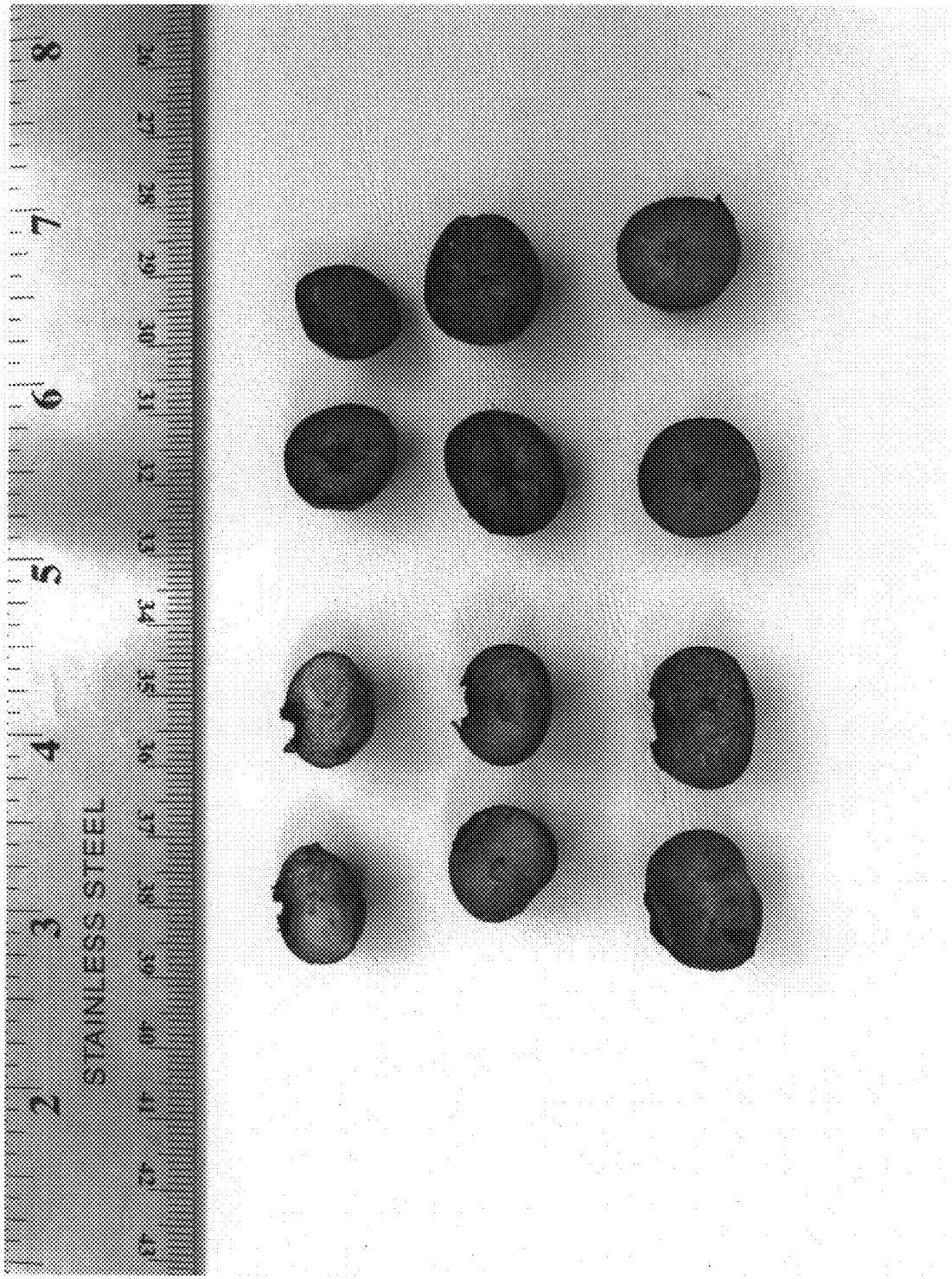
FIG. 5 illustrates cross-sections (right two columns) and longitudinal sections (left two columns) of the fruit of variety 'DrisBlueSixteen'.
Figure 6:
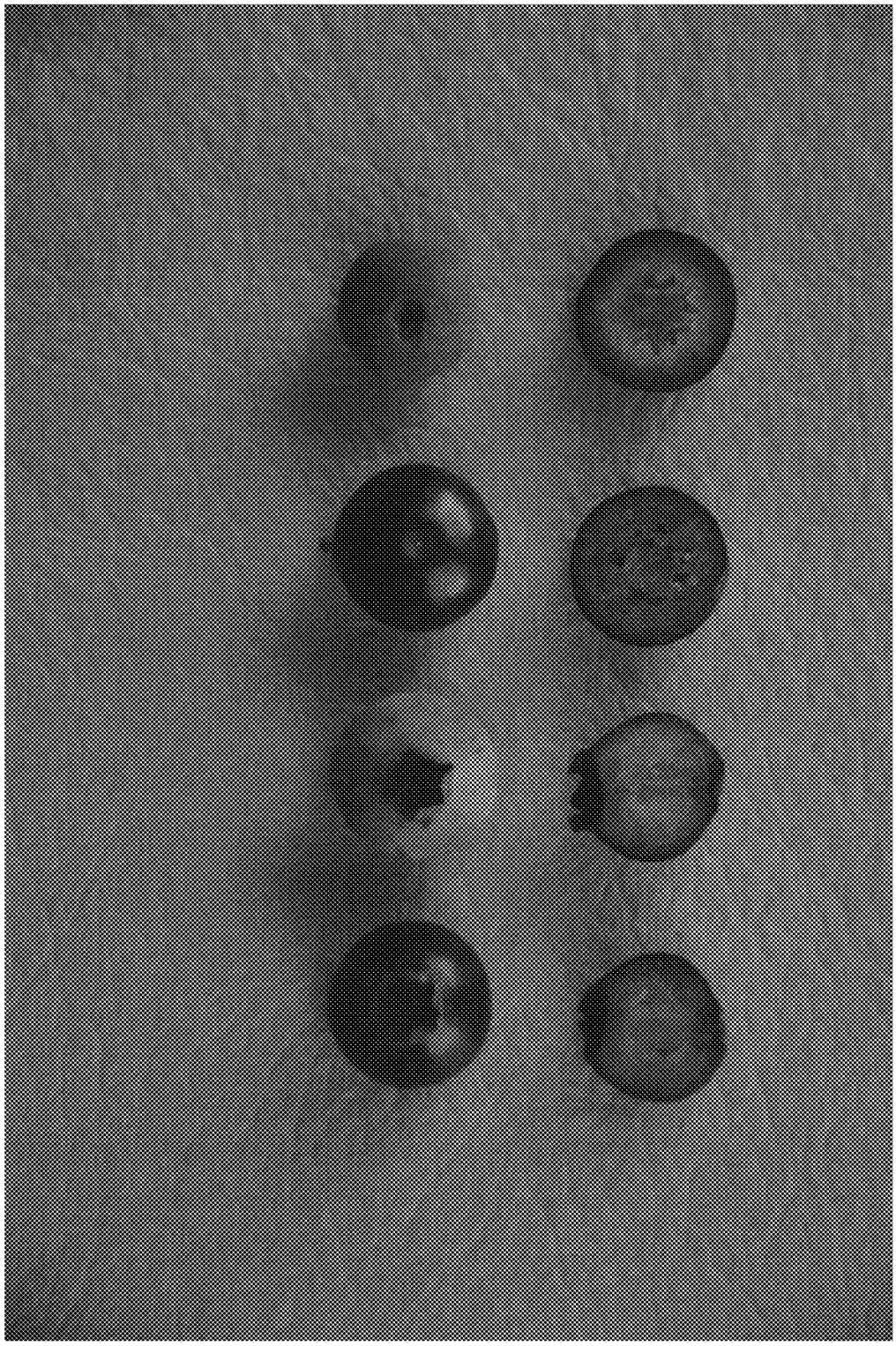
FIG. 6 illustrates whole fruit and cross-sections (right two columns) and longitudinal sections (left two columns) of the fruit of variety 'DrisBlueSixteen'. The first and third fruit on the top row (counting from left to right) have their bloom removed.
Figure 7:
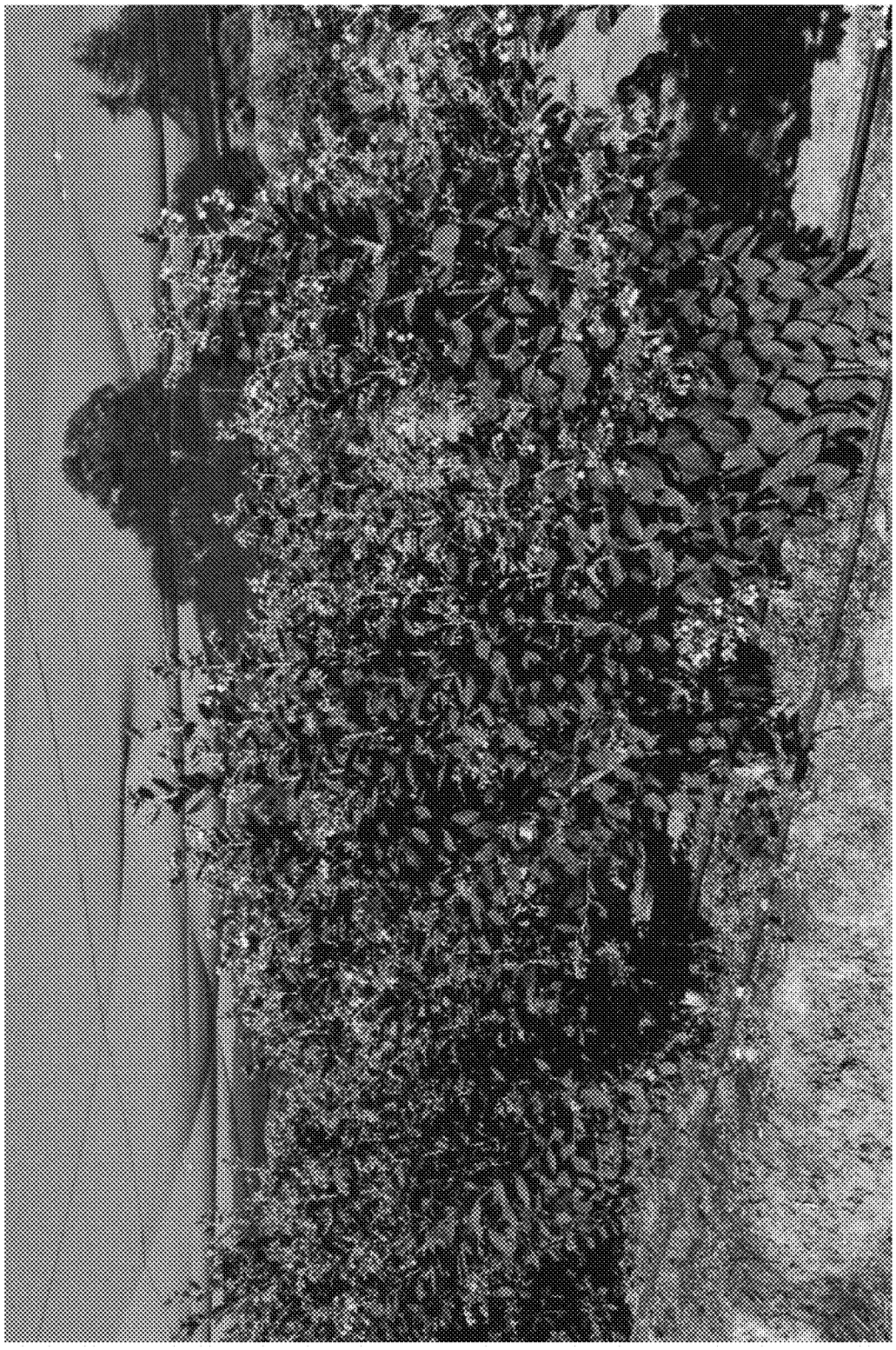
FIG. 7 illustrates plants of variety 'DrisBlueSixteen'.

The following description sets forth the distinctive characteristics of 'DrisBlueSixteen'. The data which define these characteristics is based on observations taken in Santa Cruz County and Ventura County, Calif. from 2009 to 2017. This description is in accordance with UPOV terminology. Color designations, color descriptions, and other phenotypical descriptions may deviate from the stated values and descriptions depending upon variation in environmental, seasonal, climatic and cultural conditions. 'DrisBlueSixteen' has not been observed under all possible environmental conditions. The botanical description of 'DrisBlueSixteen' was taken from 3.5-year-old plants, unless noted otherwise. The indicated values represent averages calculated from measurements of several plants. Color references are primarily to The R.H.S. Colour Chart of The Royal Horticultural Society of London (R.H.S.) (2007 edition). Descriptive terminology follows the *Plant Identification Terminology, An Illustrated Glossary, 2nd* edition by James G. Harris and Melinda Woolf Harris, unless where otherwise defined.

Classification:

*Family*.—Ericaceae.
*Botanical*.—*Vaccinium corymbosum* L.
*Common name*.—Blueberry.
*Variety name*.—'DrisBlueSixteen'.

Parentage:

*Female parent*.—The proprietary blueberry plant '127D 2' (unpatented).
*Male parent*.—The proprietary blueberry plant 'DrisBlueOne' (U.S. Plant Pat. No. 20,449).

Plant:

*Height*.—143.4 cm.
*Width*.—125.3 cm.
*Length/width ratio*.—1.1.
*Growth habit*.—Upright.
*Internode length*.—12.16 mm.
*One-year-old canes* (*young canes*).—Length: 114.6 cm. Diameter at the base: 12.6 mm. Diameter at the tip: 3.5 mm. Internode length on the upper half: 27.9 mm. Color: RHS 143D (Light green).
*Five-year-old canes* (*mature canes*).—Length: 137.3 cm. Diameter at the base: 25.8 mm. Diameter at the tip: 2.6 mm. Five-year-old cane surface texture: Rough. Five-year-old cane color: RHS 198B (Light greyed-green).

Leaves:

*Length*.—75.2 mm.
*Width*.—37.9 mm.
*Length/width ratio*.—2.0.
*Shape*.—Elliptic.
*Margin*.—Entire.
*Color on upper side*.—RHS 139A (Dark green).
*Color of lower side*.—RHS 191A (Medium greyed-green).
*Shape of the leaf apex*.—Acute.
*Shape of the leaf base*.—Cuneate.
*Petiole*.—Length: 4.8 mm. Diameter: 2.12 mm. Petiole color: RHS 144B (Medium yellow-green).

Flowers:

*Inflorescence length*.—Short.

*Length of flower* (*excluding peduncle*).—16.39 mm.

*Diameter of flower*.—8.63 mm.

*Length/width ratio*.—1.9.

*Flower bud*.—Length: 12.30 mm. Width: 4.02 mm. Number of flowers per bud: 5.90. Flower bud anthocyanin color: RHS 68B (Light red-purple).

*Pedicel*.—Length: 5.61 mm. Diameter: 1.39 mm. Pedicel color: RHS 145B (Light yellow-green).

*Peduncle*.—Peduncle color: RHS 147D (Moderate yellow-green).

*Corolla*.—Shape: Urceolate. Anthocyanin coloration of corolla tube: Absent. Ridges on corolla tube: Present. Petal width (ridge to ridge): 5.66 mm. Diameter of corolla aperture: 4.08 mm. Corolla color: RHS 155B (White).

*Sepal*.—Sepal color: RHS 144D (Light yellow-green).

*Reproductive organs*.—Style length (including stigma): 9.42 mm. Style color: RHS 141D (Medium green). Ovary color: RHS 196B (Light greyed-green). Pollen color: RHS 5C (Light yellow). Anther color: RHS N167A (Dark greyed-orange).

*Flowering interval on one-year shoot*.—June to December.

*Flowering interval on current season's shoot*.—June to December.

*Pollinator requirement*.—Insect pollinators such as honeybees or bumblebees are recommended.

Fruit:

*Length*.—12.40 mm.

*Diameter*.—14.06 mm.

*Length/width ratio*.—0.9.

*Shape in longitudinal section*.—Oblate.

*Attitude of sepals*.—Erect.

*Type of sepals*.—Reflexed.

*Calyx basin*.—Diameter: 6.52 mm. Depth: 3.39 mm. Diameter/depth ratio: 1.9.

*Weight*.—2.5 g.

*Number of berries per cluster*.—5.9.

*Peduncle* (*stalk of a fruit cluster*) length.—15.90 mm.

*Diameter of pedicel* (*stalk of a single fruit*).—1.46 mm.

*Seed*.—Length: 1.74 mm. Width: 1.16 mm. Length/width ratio: 1.5. Seed color: RHS 165B (Medium greyed-orange).

*Color of unripe fruit*.—RHS 138D (Light green).

*Color of fruit skin* (*with bloom*).—RHS 97B (Medium violet-blue).

*Color of fruit skin* (*after removal of bloom*).—RHS N186A (Dark greyed-purple).

*Intensity of fruit bloom*.—Medium.

*Color of fruit flesh*.—RHS 145B (Medium yellow-green).

*Fruit firmness*.—Medium.

*Fruit acidity*.—Medium.

*Fruit sweetness*.—Medium.

*Fruiting type*.—On one-year-old and current season's shoots.

*Ripening interval on one-year-old shoot*.—March to May.

*Ripening interval on current season's shoot*.—August to December.

*Market use of fruit*.—Fresh market.

*Fruit storage life*.—Following harvest, fruit have been stored for 21 days when maintained under cooled temperatures that are standard for blueberry storage.

*Yield*.—6000 kg/hectare to 15,000 kg/hectare of fruit per season from 48-month-old plants when grown in Santa Cruz County, Calif.

Resistance to abiotic stress, pests, and diseases:

*Drought*.—Moderately resistant.

*Heat*.—Susceptible.

*Spotted-wing drosophila* (*drosophila suzukii*).—Moderately susceptible.

*Botryosphaeria stem blight*.—Susceptible.

COMPARISONS TO PARENTAL AND COMMERCIAL BLUEBERRY VARIETIES

'DrisBlueSixteen' differs from the proprietary female parent '127D 2' (unpatented) in that fruit of 'DrisBlueSixteen' mature earlier and without chilling required when compared to fruit of '127D 2'.

'DrisBlueSixteen' differs from the proprietary male parent 'DrisBlueOne' (U.S. Plant Pat. No. 20,449) in that fruit of 'DrisBlueSixteen' mature earlier, are larger, and have a less concentrated harvest season when compared to fruit of 'DrisBlueOne'.

In addition, 'DrisBlueSixteen' differs from commercial blueberry plant variety 'DrisBlueOne' (U.S. Plant Pat. No. 20,449) in that plants of 'DrisBlueSixteen' have an upright growth habit, whereas plants of 'DrisBlueOne' have a semi-upright growth habit. Leaves of 'DrisBlueSixteen' are narrow, whereas leaves of 'DrisBlueOne' are broad. Further, unripe fruit of 'DrisBlueSixteen' have a light intensity of green color, whereas unripe fruit of 'DrisBlueOne' have a medium intensity of green color. Additionally, fruit of 'DrisBlueSixteen' have a medium intensity of bloom, whereas fruit of 'DrisBlueOne' have a strong intensity of bloom.

'DrisBlueSixteen' differs from commercial blueberry plant variety 'DrisBlueSeven' (U.S. Plant Pat. No. 24,605) in that plants of 'DrisBlueSixteen' have an upright growth habit, whereas plants of 'DrisBlueSeven' have a semi-upright growth habit. Fruit of 'DrisBlueSixteen' have a reflexed type of sepals, whereas fruit of 'DrisBlueSeven' have an incurving type of sepals. Further, fruit of 'DrisBlueSixteen' are medium in firmness, whereas fruit of 'DrisBlueSeven' are very firm in firmness. Additionally, 'DrisBlueSixteen' has a fruiting type of fruiting on one-year-old and current season's shoots, whereas 'DrisBlueSeven' has a fruiting type of fruiting on one-year-old shoots.

What is claimed is:

1. A new and distinct variety of blueberry plant designated 'DrisBlueSixteen' as shown and described herein.

* * * * *